United States Patent [19]

Angstadt et al.

[11] E Re. 30,464

[45] Reissued Dec. 30, 1980

[54] AMMOXIDATION PROCESS

[75] Inventors: Howard P. Angstadt, Media, Pa.; Jack D. Tinkler, Corona del Mar, Calif.; Richard V. Norton, Dublin, Ohio; Ronald D. Bushick, Glen Mills, Pa.

[73] Assignee: Sun Ventures, Inc., Radnor, Pa.

[21] Appl. No.: 945,358

[22] Filed: Sep. 25, 1978

Related U.S. Patent Documents

Reissue of:

[64] Patent No.: 4,070,393
Issued: Jan. 24, 1978
Appl. No.: 691,757
Filed: Jun. 1, 1976

U.S. Applications:

[63] Continuation-in-part of Ser. No. 559,617, Mar. 18, 1975, abandoned.

[51] Int. Cl.[2] ..... C07C 120/14

[52] U.S. Cl. ..... 260/465 C; 260/464; 260/465.3

[58] Field of Search ..... 260/465 C, 465.3, 464

[56] References Cited

U.S. PATENT DOCUMENTS

| | | | |
|---|---|---|---|
| 3,118,927 | 1/1964 | Foster | 260/465.3 |
| 3,501,517 | 3/1970 | Hughes et al. | 260/465 C |

FOREIGN PATENT DOCUMENTS 1453149 8/1966 France .

*Primary Examiner*—Dolph H. Torrence
*Attorney, Agent, or Firm*—J. Edward Hess; Donald R. Johnson; Paul Lipsitz

[57] ABSTRACT

In an ammoxidation process where reactant gases comprised of a lower alkyl-substituted aromatic hydrocarbon, oxygen, and ammonia are passed over an ammoxidation catalyst in a fixed or fluidized bed system, the improvement of reducing combustion of hydrocarbon and ammonia and achieving a more favorable product distribution by distributing a stream containing reactant oxygen throughout the catalyst bed.

9 Claims, 6 Drawing Figures

AMMOXIDATION PROCESS

Matter enclosed in heavy brackets [ ] appears in the original patent but forms no part of this reissue specification; matter printed in italics indicates the additions made by reissue.

CROSS REFERENCE TO RELATED APPLICATION

This application is a continuation-in-part of Ser. No. 559,617, filed Mar. 18, 1975, and now abandoned.

The vapor phase ammoxidation of organic compounds to nitriles is well known and is exemplified by U.S. Pat. No. 2,463,457 (Denton, assigned to Socony-Vacuum Oil Company, issued Mar. 1, 1949 Cl. 260-465) and by U.S. 2,496,661 (Denton, assigned to Socony-Vacuum Oil Company, issued Feb. 7, 1950; Cl. 260-465). This process is particularly useful for preparing nitriles of alkyl-substituted aromatic hydrocarbons, as for example, conversion of toluene to benzonitrile, xylenes to tolunitriles and phthalonitriles, and the like, and is also of value generally for converting alkyl-substituted aliphatic, aromatic, alicyclic, and heterocyclic compounds to the corresponding nitriles.

In carrying out the process of the prior art a catalyst is used and may be employed in either a fixed or fluidized bed mode. A preferred catalyst may be an oxide, salt, or acid of vanadium, molybdenum, tungsten or their mixture (see, for example, U.S. Pat. No. 2,496,661). In starting up the process the art teaches that the catalyst should be conditioned in order to have initial maximum catalytic efficiency and this is done by exposing it to ammonia, hydrogen, or both for a period of time, usually several minutes to several hours. Then, the process is started by passing the reactant stream composed of organic reactant, ammonia, and oxygen (or an oxygen containing stream) over the catalyst under reaction conditions.

One of the problems inherent in an ammoxidation system employing oxygen in the reactant stream as discussed above is the undesirable burn of the organic hydrocarbon reactant and ammonia to unwanted byproducts rather than nitrile products. This, of course, adds to process costs in that more reagent is required to produce a given amount of nitrile (e.g., yields are reduced) and also larger capital investment is required to build commercial sized plants. This problem with ammonia and hydrocarbon burn is particularly acute when a fixed or fluidized bed system is employed under pressure conditions.

It has now been found that ammonia and hydrocarbon burn in fixed or fluidized bed ammoxidation systems may be significantly mitigated by employing means to reduce the exotherms that tend to occur within the reactor bed. These exotherms are "hot spots" which occur within and along the bed due to localized conditions which result in very fast and very high temperature increases. In addition to alleviating this "hot spot" problem, this invention provides an unexpected higher dinitrile to mononitrile ratio and this is particularly desirable when making the dinitriles used as intermediates to aromatic dibasic acids (e.g., terephthalic acid from terephthalonitrile). These results may be achieved by a number of techniques which will be detailed further and which comprise the various embodiments of the invention.

In its broad embodiment, the invention comprises the operation of an ammoxidation reactor where a lower alkyl-substituted hydrocarbon, ammonia, and oxygen (or an oxygen containing gas) are contacted with an ammoxidation catalyst in a fixed or fluidized bed at ammoxidation conditions, and means are provided to distribute the oxygen throughout the bed such as feeding the oxygen to the fixed or fluidized bed reactor at a multiplicity of positions within the bed. Various techniques illustrating this technique will be discussed and it will be understood that where the oxygen reactant is referred to in the specification and claims it will include the use of an oxygen containing gas such as air.

Figure 1:
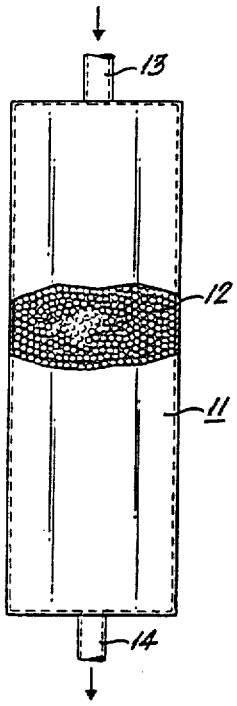
FIG. 1. (PRIOR ART)
FIG. 1 is a simplified cross-sectional view of a conventional fixed bed ammoxidation reactor.

Referring now to the drawings, it will be seen that FIG. 1 illustrates a conventional fixed bed catalytic reactor where a container 11 is filled with catalyst 12. Reactants for the ammoxidation (e.g., hydrocarbon, ammonia and oxygen) are fed into the reactor at the inlet 13 and products taken from the outlet 14.

Figure 2:
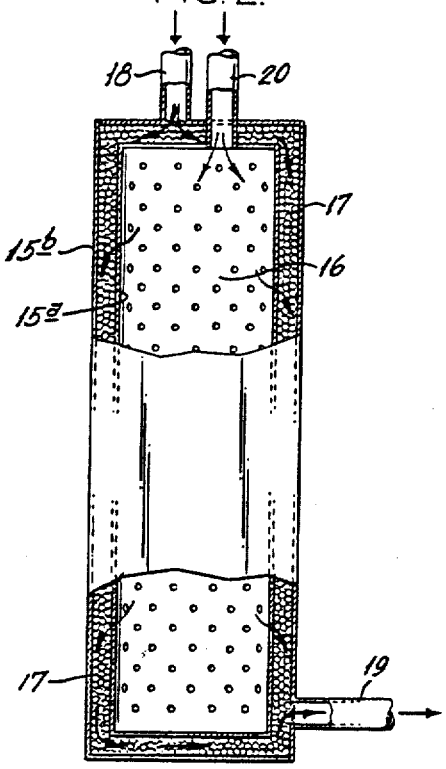
FIG. 2 is a cross-sectional view of a fixed bed reactor in accord with the invention where oxygen is introduced through porous walls.

FIG. 2 illustrates one embodiment of the invention where a double walled container provides a hollow center section (16) and has catalyst 17 distributed around the periphery of the container between the inner wall 15a and outer wall 15b. An inlet 18 for reactants leads the reactant gases over the over the catalyst 17 and the reacted gases pass through exit 19. In the apparatus of FIG. 2 the wall surrounding the hollow section is porous or permeable. The oxygen, or oxygen containing stream (such as air) is fed into the system at port 20, the remaining reactants (e.g., ammonia and hydrocarbon) being introduced at inlet 18. The oxygen thus permeates through the inner wall 15a and is thus distributed throughout the length of the catalyst bed where reaction occurs.

Figure 3:
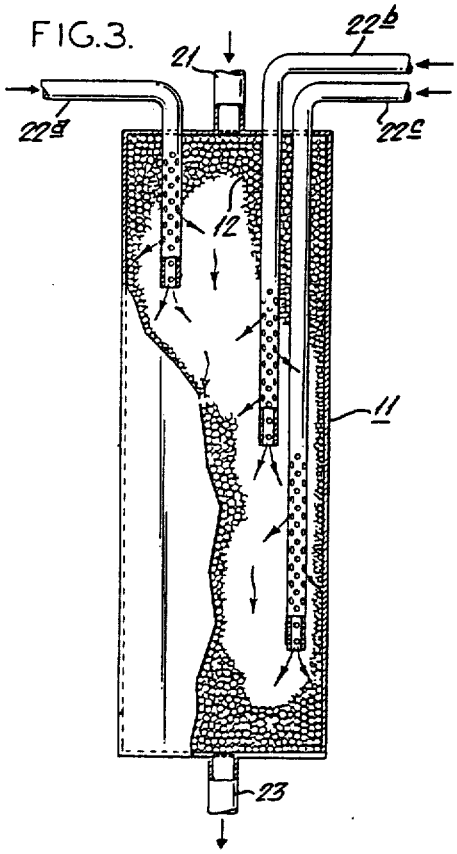
FIGS. 3 and 4 are cross-sectional views of fixed bed reactors of the present invention where oxygen is introduced at a multiplicity of positions along the length of the reactor.

In FIG. 3 another embodiment of the invention is shown. In this embodiment a reactant gas, preferably oxygen, is introduced at various levels of the reactor bed. Thus, as shown a container 11 is filled with catalyst 12 and reactant hydrocarbon and ammonia gases enter through the inlet 21. The oxygen reactant is fed into the reactor bed through several inlets 22a, 22b, and 22c which brings the oxygen to various points within the catalyst bed. The oxygen or air stream may be cooled, if desired, or it may be introduced at ambient or reaction temperature and this will be dictated by the engineering considerations and the degree of cooling desired within the bed. Usually ambient to reaction temperatures will be used for the oxygen containing stream. The product gases exit at port 23.

Figure 4:
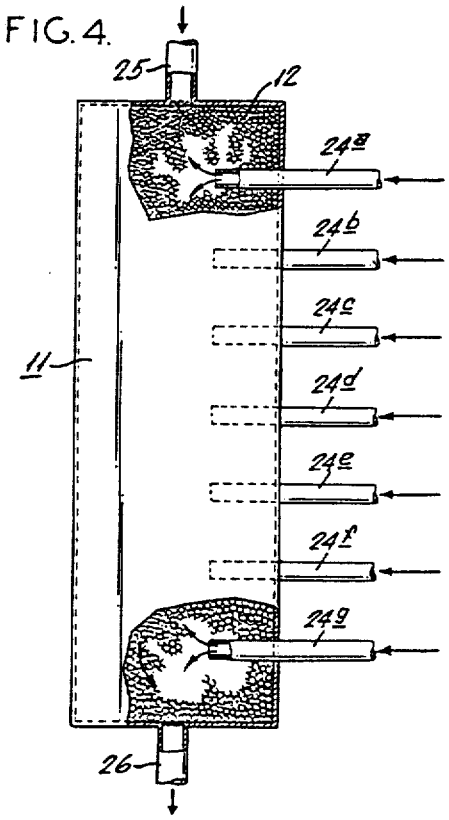

FIG. 4 shows an alternative technique where the oxygen reactant is passed into the reactor through several spaced apart side inlets 24a to 24g. As shown the catalyst 12 is held in a container 11 and input gases (e.g., hydrocarbon and ammonia) are fed through inlet 25 and product gases exit through port 26. It will be understood that the inlets 24a to 24g may be, and are preferably, valved (not shown) thereby making possible precise temperature control within the reactor.

By use of a porous wall or several streams of oxygen as described above, the bed temperature is moderated and exotherms within the bed which lead to excessive hydrocarbon and ammonia burn are alleviated.

Figure 5:
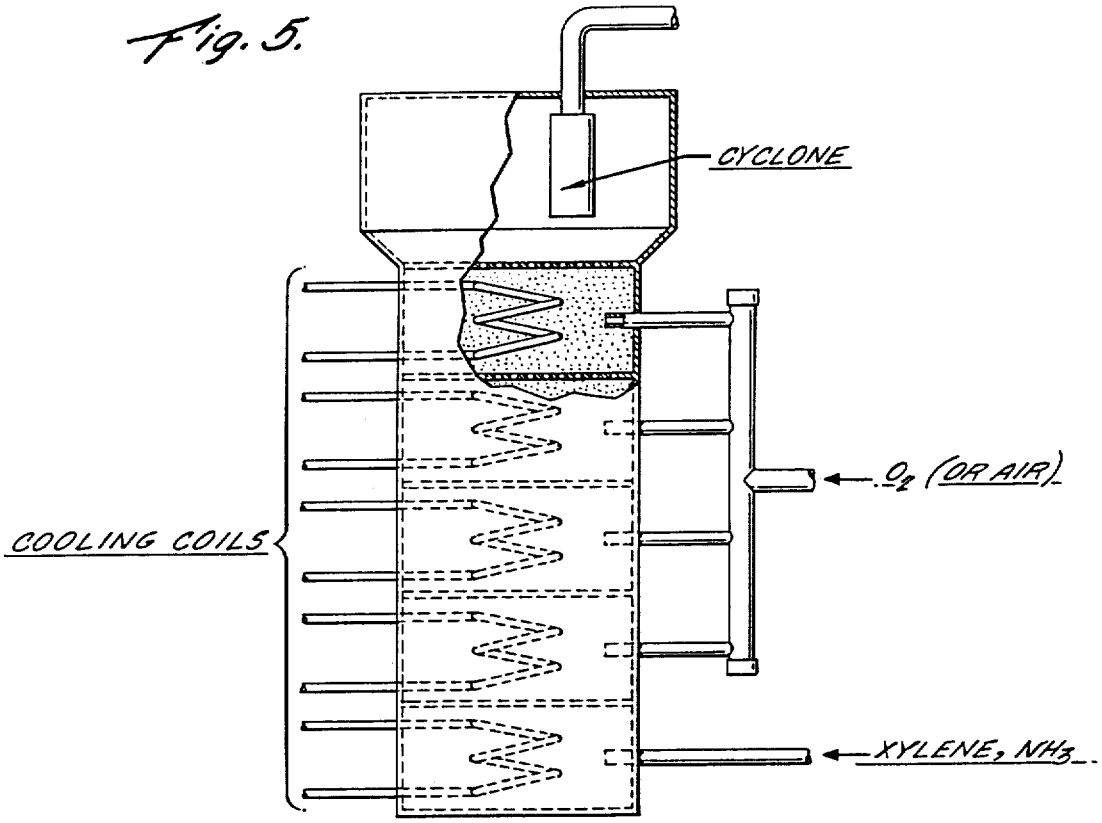
FIG. 5 is a simplified cross-sectional view of a fluidized bed reactor of cylindrical configuration where oxygen is introduced at a multiplicity of positions along the length of the reactor.

FIG. 5 shows how the technique of the invention is used with a fluidized bed system. The reactant gases xylene and ammonia are fed to the bottom of the reactor as shown and serve to fluidize the catalyst. Oxygen or air is passed into the fluidized bed at various positions along the bed and the products and unreacted gases pass through the cyclone separator at the top of the reactor where separation of catalyst fines is made to occur.

Figure 6:
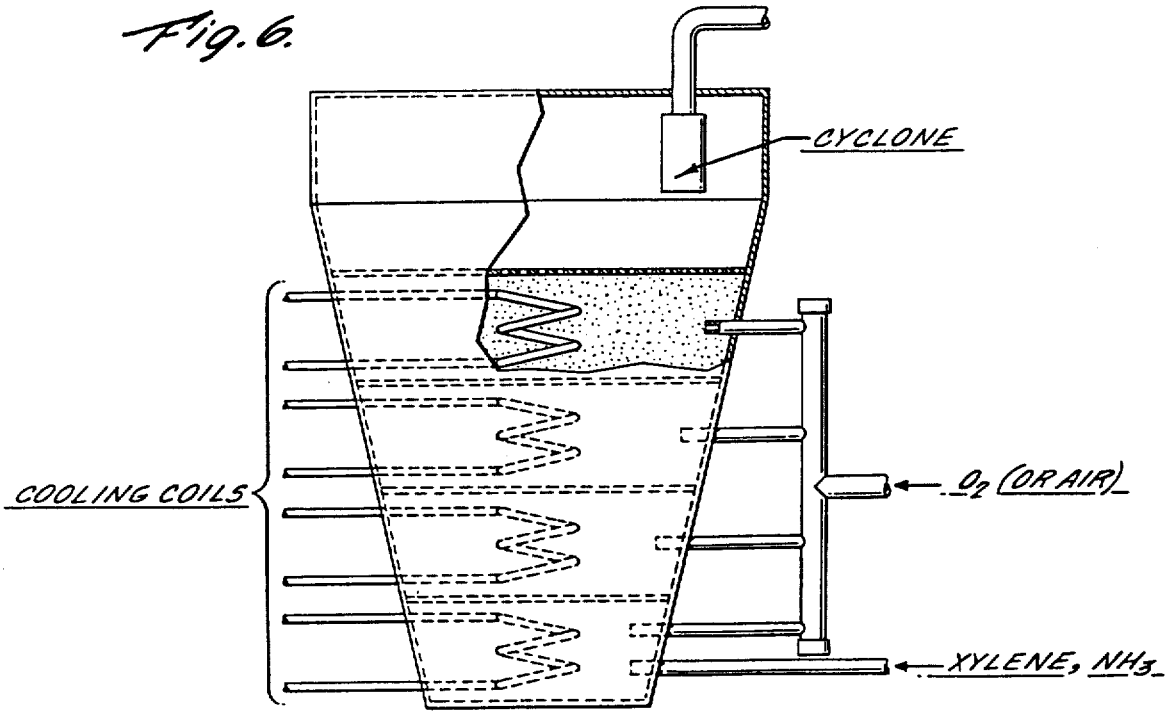
FIG. 6 is a preferred embodiment of a fluidized bed reactor where the reactor configuration is conical.

In FIG. 6 a preferred fluidized bed apparatus is shown which is conical in shape and, as before, the oxygen or air is passed into the system at spaced apart inlets along the bed. The conical shape for the fluidized bed enables maintenance of a nearly constant gas velocity and hence a more favorable degree of fluidization in the reactor. It is also desirable, and preferred when using a fluidized bed system, to use a baffled bed as described in U.S. Pat. No. 2,893,849 as such a system results in a more desirable gas residence-time distribution and results in more favorable yields.

The preferred technique as indicated above by which the usual exotherms within the bed will be reduced will be to introduce all of the required oxygen to the bed at a multiplicity of points along the bed. Furthermore, the process of the invention is particularly useful when used under pressure conditions of about 2 to about 10 atmospheres, preferably from about 2 to about 5 atmospheres.

The process of the invention will be carried out under the usual ammoxidation conditions and with any of those organic reactants which are conventionally ammoxidized to nitriles thus, the organic reactants useful in the process may be selected from a wide variety of compounds and will include alkyl-substituted aromatic, aliphatic, and alicyclic compounds. Among preferred starting materials are the mono- and polyalkyl-substituted aromatic hydrocarbons of the benzene and naphthalene series such as toluene, the xylenes, α-methylnaphthalene, polymethylnaphthalenes, (e.g., 2,6-dimethylnaphthalene), monoalkyl- and polyalkylanthracenes, mesitylene, durene, pseudocumene, methyltetralin, and the like. The alkyl substituent will be preferably methyl, but may, of course, contain more than a single carbon atom and thus the corresponding ethyl and other lower alkyl substituents are also useful.

Aliphatic compounds normally subjected to ammoxidation include the olefinic compounds. Thus, amy olefinic hydrocarbon having at least one alkyl group is useful in the process. Examples of such compounds are propylene, butenes, octenes, methyl heptenes, alkylbutadienes, pentadienes, ethyl butenes, hexadienes, heptadienes, and the like all of which will give the corresponding nitriles. Preferred olefins are those containing up to about ten carbon atoms, particularly propylene, butenes, and the methylbutadienes and cycloolefinic compounds, particularly the alkyl-substituted hydrocarbon olefins exemplified by 2-methylcyclohexene, 1,2-dimethylcyclohexene, and the like.

Also of value as reactants are alicyclic compounds having an alkyl substituent and these compounds are exemplified by methylcyclopentane, methylcyclohexane, the alkyl-substituted decalins, and the like.

The catalyst used in the process of the invention will comprise any of the conventional ammoxidation catalysts. For example, the catalyst will comprise one or more elements selected from copper, silver, tin, uranium, thorium, vanadium, chromium, molybdenum, tungsten or the metals of Group VIII of the Periodic Table according to Mendeleev or one or more of the compounds, preferably the oxide, of any of said elements. Catalysts used in the process of the invention may be employed without a support, but, preferably, are supported on an aluminous or siliceous carrier or support.

Suitable alumina carriers and siliceous carriers include, for example, alumina gel, activated alumina, α-alumina, silica gel, carborundum, diatomaceous earth, pumise, acid clay and asbestos. The catalyst may be formed on the support by any convenient method, for example, the coprecipitation method or immersion method employing the nitrates, chlorides, oxides, hydroxides, organic acid salts or, in the case of those elements which may form a part of an anion, the acid containing these metals or the alkali or ammonium salts of the acid. The catalyst to be supported may be a single metal or a plurality of metals or it may consist of a mixture of the metal compounds; e.g., the oxides.

In a preferred embodiment of the invention a particular type of material known as a vanadium bronze preferably supported on α-alumina will be used as catalyst. It is known in the art that the addition of an alkali mwetal compound to vanadium pentoxide will, when the mixture is heated, yield complex materials with anomalous valencies known as a vanadium bronzes and such materials are described in the literature, as, for example, the article by P. Hagenmuller entitled "Tungsten Bronzes, Vanadium Bronzes and Related Compounds" at pages 541 to 605 of "Comprehensive Inorganic Chemistry", edited by J. C. Bailar, Jr., et al. and published in 1973 by Pergamon Press.

The amount of catalyst on the support (e.g., catalyst loading) will be from about 1 to about 15 percent by weight, preferably about 3 to 8 percent. The surface area of the preferred catalysts used in the process is generally quite low being less than 10 $m^2$ per gram and usually 1 to 5 $m^2$ per gram. Pore volume of the catalyst is such that the major proportion of the pores have diameters less than about 1 micron, being on the order of about 0.2 to 1.0 micron.

As indicated, the process of the invention is carried out in a fixed or fluidized bed mode of operation at a temperature between about 350° and about 525° C., preferably 390° to 500° C. The source of oxygen is preferably air, but any oxygen source is suitable. The amount of oxygen used in the process may vary over a wide range, say from about 0.5 to about 10 moles of oxygen per mole of hydrocarbon. In a preferred technique an oxygen to p-xylene ratio of no more than about 3:1, preferably 2.5:1 to 3:1 will be used, although about 2:1 is also quite useful. Likewise the molar ratio of ammonia to hydrocarbon used in the process may vary widely and be from about 1 to about 10, but in a preferred embodiment will by about 3:1 or less, preferably about 2:1 to 3:1. In the preferred method, the volume percent concentration of reactants corresponding to the above preferred ratios will also be quite high as compared to most ammoxidation procedures and the feed will comprise in percent by volume 6 to 7 percent p-xylene, 13 to 18 percent oxygen, and 10 to 22 percent ammonia.

It will be understood that the hydrocarbon contact time for the reactants over the catalyst will vary over a wide range, but will usually be from about 0.1 to 20 seconds. The contact time actually used will depend upon catalyst loading, catalyst volume, temperature and other parameters and the skilled art worker will have no difficulty in selecting an appropriate contact time dependent upon these reaction parameters.

As indicated, the process is of greatest significance when operated under pressure conditions since pressure operation of a fixed bed ammoxidation system causes a reduction of yield of nitrile product due to excessive burning of hydrocarbon and ammonia. Thus, the process of the invention will be operated preferably at a pressure of from about 1.5 to about 4 atmospheres as this is consistent with efficient operation at minimum capital expense.

The process of the invention will most preferably be carried out with lower alkyl-substituted aromatic hydrocarbons of the benzene and naphthalene series; e.g., toluene, m-xylene, p-xylene, 2,6-dimethylnaphthalene, 1,4-dimethylnaphthalene, and the like.

Both meta- and para-xylene are particularly useful reactants for the process. When using m-xylene to obtain isophthalonitrile, however, it is preferred to employ temperatures at the lower end of the range given above and this is in accord with art knowledge that m-xylene is more sensitive to carbon oxide formation than is the p-isomer.

It will be understood also that the unreacted hydrocarbon and mononitrile by-products will be recycled to the reactor in order to increase efficiency, and the mononitrile recycle being of particular value for increased conversion of hydrocarbon to dinitrile. In order to further describe and illustrate the invention the following examples are given illustrating the preferred catalysts and process conditions:

EXAMPLES 1 to 3

Using equipment as described in FIG. 3 and for a control run, a conventional fixed bed reactor as in FIG. 1, an ammoxidation of p-xylene was carried out using a vanadium oxide catalyst supported on alumina with air as the source of oxygen. The following table gives the reaction conditions of mole ratios of reactants to hydrocarbon (HC), temperature, and contact time and the results obtained.

reactants and passed together into the conventional reactor, the amount of dinitrile (TPN) was significantly less than when the oxygen was entered into the bed at various levels in accord with the invention. It is to be noted also that in comparing Example 1 with the control where the $NH_3$/HC ratios, temperatures and contact times are comparable, the process of the invention gave a total nitrile product (TN+TPN) of 92.0 percent versus 82.2 percent for the control.

EXAMPLES 4 to 5

A one-inch O.D. reactor with side inlets for air addition similar to the apparatus of FIG. 4 is used for ammoxidation of p-xylene. This reactor contains a 19 inch long section of sodium vanadium bronze catalyst (8 percent loading) preceded and followed by sections of quartz chips. The catalyst has the empirical formula $Na_xV_2O_5$ (where X=0.7 to 1.0) and is supported on $\alpha$-alumina. The top quartz zone which acts as a preheater is above the sand level in a fluidized sandbath so that temperatur can be controlled separately via an electrical winding. The reactor tube has seven air inlets spaced equidistantly (2⅜ inches apart) along the reactor length. Each of these inlets is fed through a separate rotameter so that uniform air flows are obtained to all inlets. The reactor is equipped with a ⅛ inch thermowell and traveling thermocouple running the entire reactor length.

Two runs at about 30 psig pressure were made in this reactor with multiple air injection. The reaction conditions and results are shown in the following Table II where they are compared to a control run made with normal air addition (i.e., all of the air enters at reactor inlet).

TABLE II

| Example Number | Control | No. 4 | No. 5 |
|---|---|---|---|
| Air Addition | Normal | Multiple | Multiple |
| Sand Bath Temp., °C. | 400 | 400 | 370 |
| $O_2$/HC Mole Ratio | 2.5 | 2.5 | 2.5 |
| $NH_3$/HC Mole Ratio | 2.5 | 2.5 | 2.5 |
| Pressure, psig | 30 | 30 | 30 |
| PX Contact Time, Seconds | 8 | 10.4 | 10.4 |
| Single-pass PX Conversion, % | 14 | 68 | 57 |
| Single-pass Selectivity, % | | | |
| TN | 16 | 55 | 55 |
| TPN | 1 | 34 | 34 |
| TN + TPN | 17 | 89 | 89 |
| TPN/TN + TPN | 0.058 | 0.382 | 0.382 |
| TPN Plant Yield, % | 3 | 84 | 82 |

TABLE I

AMMOXIDATION OF p-XYLENE

| Example No. | Mole Ratio $NH_3$/HC | Mole Ratio $O_2$/HC | Temp (°C.) | Contact Time (sec.) | Product Distribution, Percent | | | | | | |
|---|---|---|---|---|---|---|---|---|---|---|---|
| | | | | | CO | $CO_2$ | BN | TN | TPN | TN + TPN | TPN / TN + TPN |
| 1 | 6.0 | Note a | 450 | 5.0 | 0.6 | 6.9 | 0.5 | 38.7 | 53.3 | 92.0 | 0.579 |
| 2 | 3.0 | Note a | 450 | 5.0 | 1.4 | 9.8 | 0.9 | 49.9 | 38.0 | 87.9 | 0.432 |
| 3 | 3.0 | Note b | 450 | 5.0 | 3.8 | 15.2 | 1.3 | 47.9 | 31.8 | 79.7 | 0.399 |
| Control | 6.0 | 2.7 | 450 | 5.0 | 7.6 | 7.2 | 3.0 | 55.8 | 26.4 | 82.2 | 0.321 |

NOTES:
a. Oxygen:hydrocarbon = 3:1 (total); feed split one-half through oxygen inlet tube 22a, one-half through oxygen inlet tubes 22b and 22c (see FIG. 3).
b. Oxygen:hydrocarbon = 3:1 (total); feed split two-thirds through oxygen inlet tube 22a, one-third through oxygen inlet tubes 22b and 22c (see FIG. 3).
LEGEND:
BN = Benzonitrile
TN = Tolunitrile
TPN = Terephthalonitrile As can be seen from the above data when the oxygen was combined with the hydrocarbon and ammonia TABLE II-continued

| Example Number | Control | No. 4 | No. 5 |
|---|---|---|---|
| $NH_3$ Burn, % of $NH_3$ Feed | 52 | 16 | 18 |

Legend:
HC = hydrocarbon
PX = p-xylene
TN = tolunitrile
TPN = terephthalonitrile It is clear from the above data that the multiple air injection technique of this invention dramatically increases xylene conversion, increases the dinitrile yield, and also significantly reduces ammonia burn and thereby makes for an overall more efficient process.

EXAMPLES 6 to 8

Using the equipment illustrated in FIG. 2 where the catalyst bed is 0.25 inches thick and the center portion filled with crushed quartz, an ammoxidation with p-xylene is carried out at 30 psig pressure. In Examples 6 and 8 the catalyst used is similar to that of Examples 4 and 5. The catalyst in Example 7 is an unsupported mixture of $V_2O_5$, $TiO_2$ and $B_2O_3$ in a weight ratio of 1:1:0.125. The Table III which follows shows the reaction conditions and results and for comparison a control is included in each where the oxygen (as air) was admitted to the reactor with the hydrocarbon and ammonia.

TABLE III p-XYLENE AMMOXIDATION
($O_2$ Added Via Inner Porous Tube)

| Ex. No. | Temp | Contact Time (sec.) | Mole Ratio $NH_3$/HC | Mole Ratio $O_2$/HC | % Conv | % CO's | Product Distribution, % TN | TPN | TN + TPN | TPN / TN + TPN | % $NH_3$ Burn |
|---|---|---|---|---|---|---|---|---|---|---|---|
| 6 | 400 | 7 | 4.0 | 1.7 | 37.6 | 17.2 | 38.5 | 41.4 | 79.8 | 0.518 | 18.1 |
| Control | 400 | 7 | 4.0 | 1.7 | 17.4 | 37.6 | 28.1 | 19.1 | 47.2 | 0.405 | 35.0 |
| 7 | 425 | 6 | 4.0 | 2.0 | 39.3 | 9.3 | 46.1 | 39.2 | 85.3 | 0.459 | 22.0 |
| Control | 425 | 4 | 4.0 | 2.0 | 18.3 | 17.1 | 57.3 | 15.6 | 72.9 | 0.215 | 50.4 |
| 8 | 450 | 8 | 3.9 | 2.9 | 64.1 | 8.8 | 46.3 | 44.5 | 90.8 | 0.490 | 28.4 |
| Control | 450 | 6 | 3.0 | 3.0 | 50.6 | 17.2 | 43.4 | 37.9 | 81.3 | 0.467 | 52.4 |

The invention claimed is:

[1. In an ammoxidation process where reactant gases comprised of a lower alkyl-substituted hydrocarbon, oxygen, and ammonia are passed over an ammoxidation catalyst in a fixed or fluidized bed system, the improvement of reducing combustion of hydrocarbon and ammonia burn by distributing said reactant oxygen at a multiplicity of positions along the length of said catalyst bed.]

[2. The process of claim 1 wherein the ammoxidation is carried out under pressure of from 2 to about 10 atmospheres.]

[3. The process of claim 2 wherein the hydrocarbon is an aromatic hydrocarbon of the benzene of naphthalene series.]

[4. The process of claim 3 where the aromatic hydrocarbon is a xylene.]

[5. The process of claim 3 where the aromatic hydrocarbon is p-xylene.]

6. A process for the preparation of an aromatic dinitrile of the benzene and naphthalene series which comprises reacting a [lower] *dilower* alkyl-substituted hydrocarbon of the benzene or naphthalene series with ammonia and oxygen at a temperature of between about 350° and about 525° C. in the presence of a supported vanadium catalyst in a fixed bed, the mole ratio of ammonia to hydrocarbon being from about 2:1 to about 3:1, the mole ratio of oxygen to hydrocarbon being from about 2:1 to about 3:1, and distributing the oxygen through spaced apart inlets along the length of the bed.

7. The process of claim 6 where the hydrocarbon is p-xylene.

8. A process for the preparation of terephthalonitrile which comprises reacting p-xylene in a fixed bed mode with ammonia and oxygen at a temperature between about 390° and about 500° C. and at a pressure of from about 2 to about 10 atmospheres in the presence of a vanadium bronze catalyst said mole ratio of ammonia to p-xylene being from about 2:1 to about 3:1, the mole ratio of oxygen to hydrocarbon being from about 2:1 to about 3:1, and distributing the oxygen throughout the bed by passing said oxygen through spaced-apart inlets along the length of the bed.

9. The process of claim 8 operated at a pressure of from about 2 to about 5 atmospheres.

10. The process of claim 9 wherein said catalyst is a sodium-vanadium bronze supported on α-alumina.

11. A process for the preparation of an aromatic dinitrile of the benzene and naphthalene series which comprises reacting a [lower] *dilower* alkyl-substituted hydrocarbon of the benzene or naphthalene series with ammonia and oxygen at a temperature of between about 350° and about 525° C. in the presence of a supported vanadium catalyst in a fluidized bed, the mole ratio of ammonia to hydrocarbon being from about 2:1 to about 3:1, the mole ratio of oxygen to hydrocarbon being from about 2:1 to about 3:1, and distributing the oxygen through spaced apart inlets along the length of the bed.

12. A process for the preparation of terephthalonitrile which comprises reacting p-xylene in a fluidized bed mode with ammonia and oxygen at a temperature between about 390° and about 500° C. and at a pressure of from about 2 to about 10 atmospheres in the presence of vanadium bronze catalyst said mole ratio of ammonia to p-xylene being from about 2:1 to about 3:1, the mole ratio of oxygen to hydrocarbon being from about 2:1 to about 3:1, and distributing the oxygen throughout the bed by passing said oxygen through spaced-apart inlets along the length of the bed.

13. The process of claim 12 where the catalyst is a sodium-vanadium bronze supported on α-alumina and the pressure of the reaction is from about 2 to about 5 atmospheres.

14. The process of claim 13 where the fluidized bed is in a baffled conical reactor.

* * * * *